United States Patent
Jager Lezer et al.

(10) Patent No.: US 10,278,902 B2
(45) Date of Patent: May 7, 2019

(54) COSMETIC METHOD OF MODIFYING THE APPEARANCE OF THE OUTLINE OF THE EYE

(75) Inventors: Nathalie Jager Lezer, Verrieres-le-Buisson (FR); Henri Samain, Bievres (FR); Vincent De Laforcade, Rambouillet (FR)

(73) Assignee: L'OREAL, Paris (FR)

( * ) Notice: Subject to any disclaimer, the term of this patent is extended or adjusted under 35 U.S.C. 154(b) by 528 days.

(21) Appl. No.: 13/520,474

(22) PCT Filed: Jan. 17, 2011

(86) PCT No.: PCT/IB2011/050191
§ 371 (c)(1),
(2), (4) Date: Dec. 13, 2012

(87) PCT Pub. No.: WO2011/086530
PCT Pub. Date: Jul. 21, 2011

(65) Prior Publication Data
US 2013/0089584 A1    Apr. 11, 2013

Related U.S. Application Data

(60) Provisional application No. 61/358,136, filed on Jun. 24, 2010.

(30) Foreign Application Priority Data

Jan. 18, 2010   (FR) ...................................... 10 50288

(51) Int. Cl.
*A61K 8/02*       (2006.01)
*A45D 44/22*      (2006.01)
*A61Q 1/00*       (2006.01)

(52) U.S. Cl.
CPC ............ *A61K 8/0208* (2013.01); *A45D 44/22* (2013.01); *A61Q 1/00* (2013.01)

(58) Field of Classification Search
CPC .... A61F 9/00718; A61F 9/007; A61F 13/023; A61F 13/0246; A61F 2013/0037; A61F 9/04; A61F 13/124; A61F 2013/00497; A45D 44/22; A61B 17/00491; A61B 17/0231; A61B 5/0555; A61B 5/7285; A61B 2090/0817; A61B 5/0037; A61B 5/0263; A61B 5/029; A61B 5/0402; A61B 5/055; A61B 5/7271; A61B 5/742; C07D 519/00; C07D 471/04; C07D 491/20
See application file for complete search history.

(56) References Cited

U.S. PATENT DOCUMENTS

| | | | |
|---|---|---|---|
| 2,572,638 A | 10/1951 | Loos | |
| 4,653,483 A * | 3/1987 | Clavin | 606/204.25 |
| 4,854,307 A | 8/1989 | Elfenbein | |
| 4,969,472 A | 11/1990 | Langley | |
| 5,542,437 A * | 8/1996 | Blackmore et al. | 128/899 |
| 6,190,346 B1 | 2/2001 | McGill | |
| 2005/0061341 A1* | 3/2005 | Choe | 132/53 |

FOREIGN PATENT DOCUMENTS

| | | |
|---|---|---|
| CN | 1389164 A | 1/2003 |
| CN | 101426395 A | 5/2009 |
| JP | S5657228 U | 5/1981 |
| JP | 2001-070040 A | 3/2001 |
| JP | A-2008-308807 | 12/2008 |
| WO | WO 01/34078 A1 | 5/2001 |

OTHER PUBLICATIONS

Jul. 15, 2011 Written Opinion on the International Searching Authority issued in International Patent Application No. PCT/IB2011/050191.
Jul. 15, 2011 International Search Report issued in International Patent Application No. PCT/IB2011/050191.
Jul. 28, 2014 Office Action issued in Chinese Patent Application No. 201180006439.X (with Summary of Analysis of the First Office Action partial English translation).
Jun. 1, 2015 Chinese Office Action issued in Chinese Patent Application No. 201180006439X.
Jan. 21, 2015 Office Action issued in Japanese Application No. 2012-549447.

* cited by examiner

*Primary Examiner* — Audrea B Coniglio
(74) *Attorney, Agent, or Firm* — Oliff PLC

(57) ABSTRACT

A method of cosmetically modifying the appearance of the outline of the eye, the method including the step consisting in applying at least one patch on the movable upper eyelid, the application face of the patch having a predefined non-plane shape with multi-directional curvature, or at least one patch made of a material suitable for responding to stress by deforming in non-elastic manner as to take up multi-directional curvature on the eyelid and conserve the curvature when the stress ceases.

22 Claims, 5 Drawing Sheets

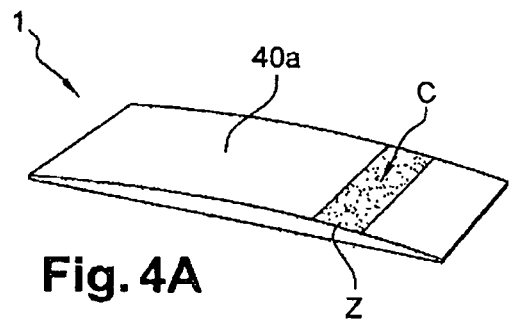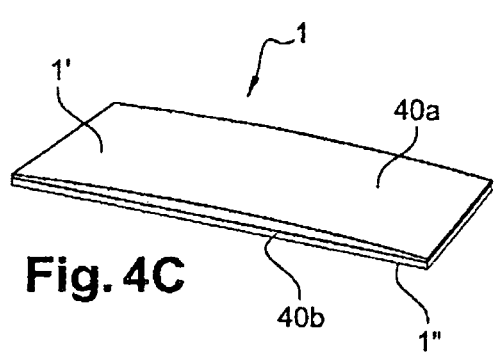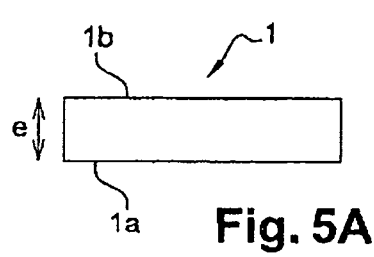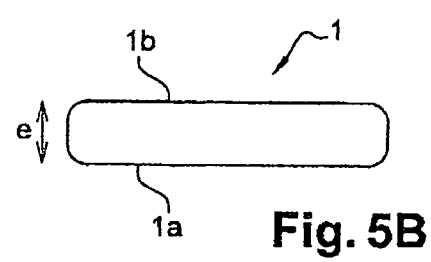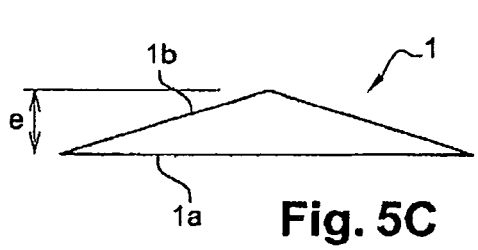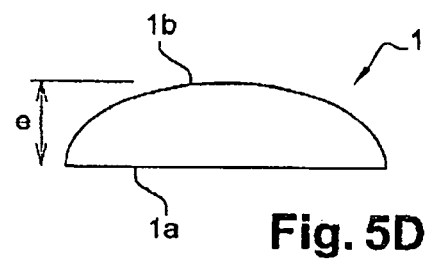

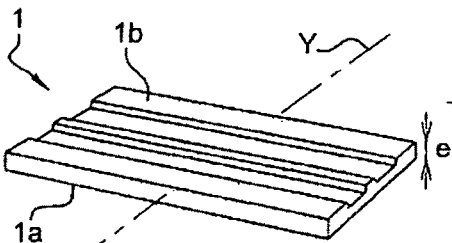
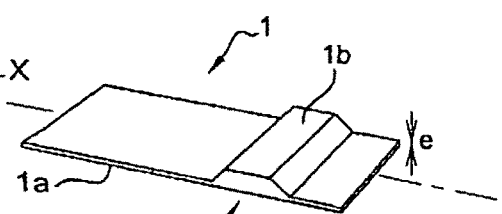
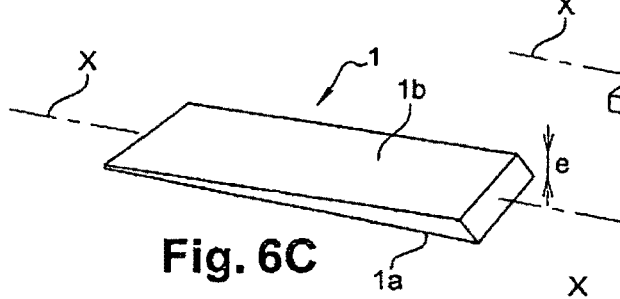
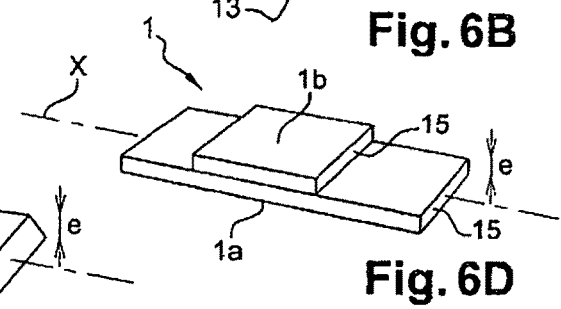
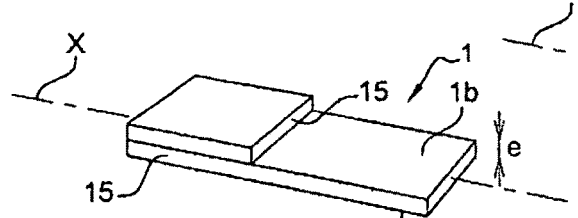
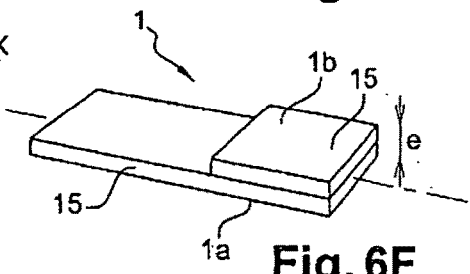
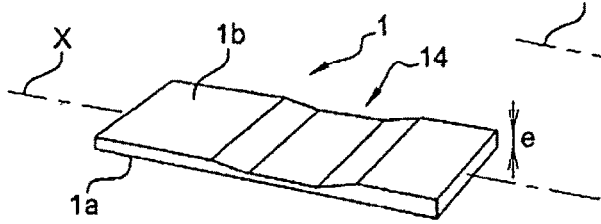
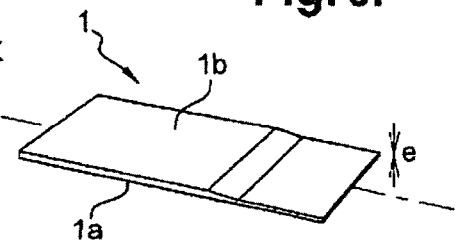
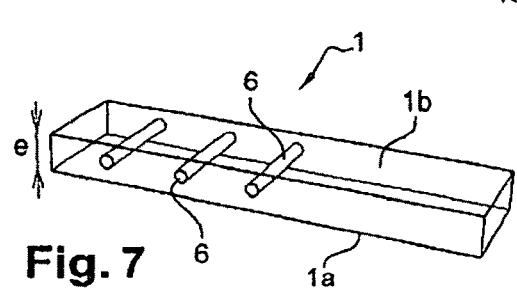
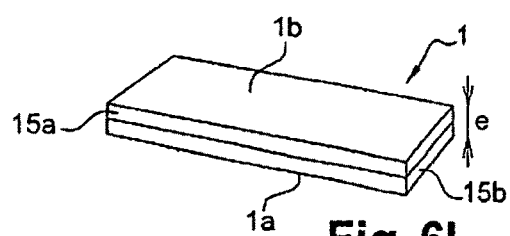

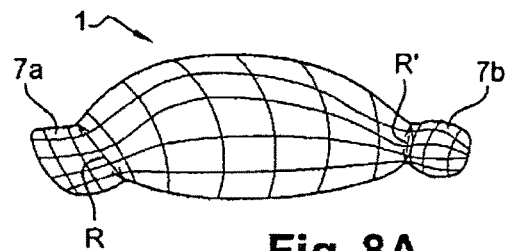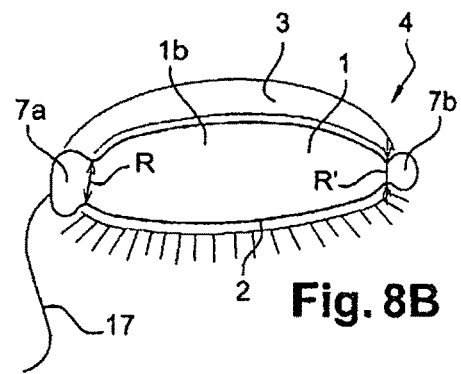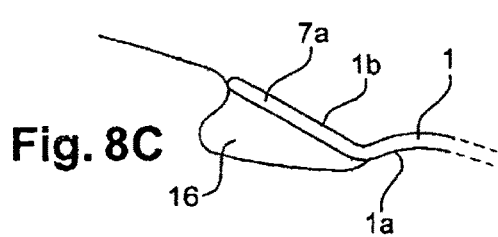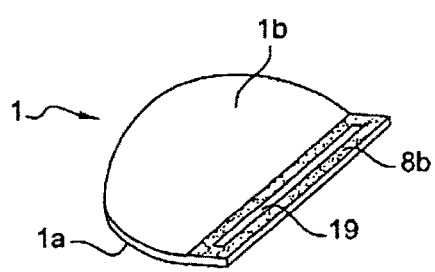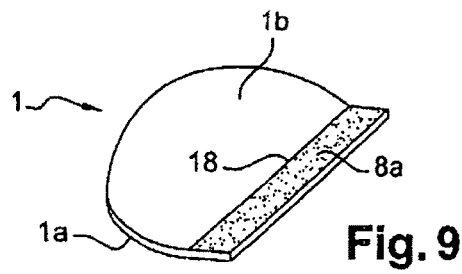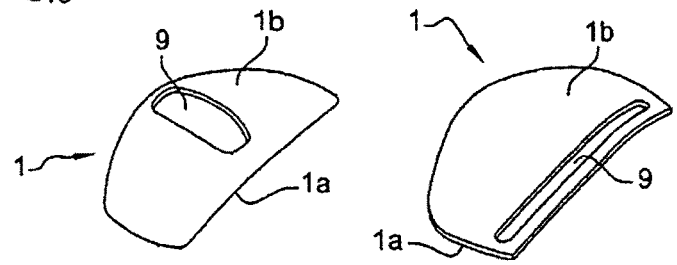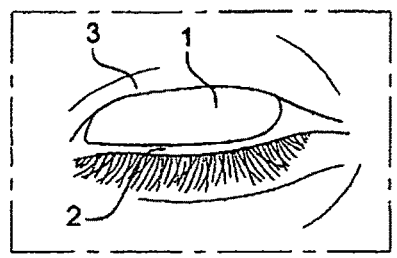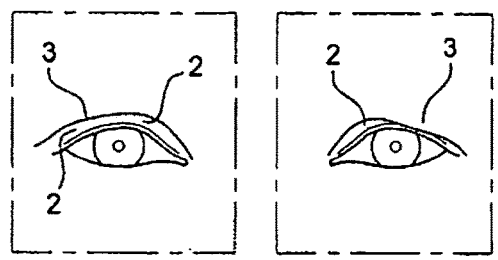

COSMETIC METHOD OF MODIFYING THE APPEARANCE OF THE OUTLINE OF THE EYE

The present invention relates to a cosmetic method of modifying the appearance of the outline of the eye, and to an associated patch and kit.

BACKGROUND

Numerous people seek to modify the appearance of the outlines of their eyes, in particular to beautify their look, e.g. in application of recognized or personal esthetic criteria, in order to change the appearance of their look or indeed to correct one or more imperfections, in particular asymmetry between their eyes, e.g. one eye being more closed than the other.

Other people may seek to restore the appearance of the outlines of their eyes to what it used to be when they were younger. One particular consequence of aging can be drooping of the stationary upper eyelid, sometimes to such an extent as to partially overlie the movable upper eyelid when the eye is open. This phenomenon is often associated by observers with the person aging and is generally perceived as being undesirable.

Finally, certain people may also desire to modify the shapes of the outlines of their eyes because of their dimensions, e.g. one eye being too closed or too open, too large or too small, or having an undesirable bulging appearance.

It is known to apply makeup compositions to the outline of the eye, in particular to emphasize all or part of the outline of the eyes in color. Nevertheless, making up the eyes presents several drawbacks. It often serves to emphasize the eyes but does not affect the shape of the outlines of the eyes. It is particularly difficult to restore asymmetries and practically impossible to look younger. Furthermore, the shading created by applying makeup is not desired by many people, in particular men, children, old people, and certain women. Applying makeup also requires a certain amount of skill in order to apply it effectively. In addition, it is often necessary to comply with certain precautions in order to maintain a makeup result over time, in particular by avoiding any rubbing or washing, and makeup generally lasts only for a few hours, or at most one or two days, so it needs to be repeated regularly.

It is possible to modify a person's look by using plastic surgery. Nevertheless, most people would prefer not to have recourse to plastic surgery, since that solution is often perceived as being too radical and is sometimes painful. Furthermore, plastic surgery does not achieve a more youthful look, and is appropriate above all for major corrective purposes, being unsuitable for minor corrective purposes or merely for satisfying the desire to change the look of the eyes.

It is known to apply elongate flat strips to the movable upper eyelid in order to form an artificial fold in the eyelid. Such strips are used in particular by people of Asiatic origin in whom the movable upper eyelid presents a palpebral fold that is less marked than for the eyes of people of Caucasian or African origin, for the purpose of making the appearance of an Asiatic eye come closer to that of a Caucasian or African eye. Nevertheless, that phenomenon hardly exists in Caucasian or African eyes, and as a result that solution has no effect on eyes of those types.

U.S. Pat. No. 4,854,307 describes applying a liquid adhesive composition to stick together the movable upper eyelid and the stationary upper eyelid. Adhesive presents the drawback of being uncomfortable and dangerous for the user, and it does not enable the look to be modified or corrected in accurate and appropriate manner for all users.

U.S. Pat. No. 6,190,346 and international application WO 01/34078 describe applying a flat adhesive strip on the movable upper eyelid in order to correct drooping of the stationary upper eyelid. That solution does not enable the outline of the eye to be modified in a manner that is as effective and as comfortable as would be desirable, since the strip is not adapted to the topology of the eyelid onto which it is applied.

SUMMARY

There exists a need to remedy at least some of the above-mentioned drawbacks.

In particular, it is desirable to be able to modify the appearance of the outline of the eye in a manner that is attractive, simple, long-lasting, effective, reversible, and adapted to eyes of all types, whether Caucasian, Asiatic, or African.

There also exists a need to find a solution that is suitable for adapting to all types of people, in particular of any age, without causing unattractive and undesirable folds to form in the skin.

In general manner, the invention relies on using a patch, also referred to as an esthetic prosthesis.

Exemplary embodiments of the invention thus provide a method of cosmetically modifying the appearance of the outline of the eye, the method comprising the step consisting in applying at least one patch on the movable upper eyelid, the application face of the patch having a predefined non-plane shape with multi-directional curvature, or at least one patch made of a material suitable for responding to stress by deforming in non-elastic manner as to take up multi-directional curvature on the eyelid and conserve said curvature when the stress ceases.

The term "multi-directional curvature" should be understood as curvature in at least two distinct planes, e.g. mutually perpendicular planes, e.g. a longitudinal plane containing the longitudinal axis of the patch and a transverse plane perpendicular thereto.

In exemplary embodiments of the invention, the method thus comprises:
- a step consisting in applying at least one patch to the movable upper eyelid, the application face of the patch having a predefined non-plane shape with double curvature prior to application; and/or
- a step consisting in applying at least one patch on the movable upper eyelid and in modifying at least one curvature of the patch after application, the patch tending by plastic deformation to conserve the shape into which it is put, independently of the movable upper eyelid.

The term "double curvature" should be understood as meaning that the application face of the patch has a shape presenting at least two curvatures about at least two distinct axes, in particular two mutually perpendicular axes, e.g. one curvature about a longitudinal axis of the patch and the other curvature about a transverse axis of the patch.

By means of the invention, the patch applied to the movable upper eyelid may present a shape that is better adapted to the shape of the movable upper eyelid, thus making it possible simultaneously to provide comfort while the patch is being worn and to facilitate utilization of the patch, depending on each person's needs.

The invention may reduce the risk of folds forming, even when applied to skin that is fine or old, or even if applied too quickly. The patch may thus be applied more easily and without taking great care.

The ergonomy of using the patch may also be improved and adapted to each individual. As a result, the patch may be put into place and removed quickly and instinctively. For example, there is less risk of placing the wrong face of the patch on the movable upper eyelid.

Furthermore, the curvature of the patch may make it easier for the patch to adhere to the movable upper eyelid, thus making it possible under some circumstances to secure the patch without using an adhesive, e.g. merely by surface tension, or using an adhesive having low adhesive power. This may make it easier to remove the patch, may irritate the skin less, may stay in place better over time, and/or may make it easier to reposition the patch on the movable upper eyelid.

The patch may be of stiffness and/or thickness that vary, e.g. in order to obtain better effects in lifting the stationary upper eyelid, for example.

The patch may be pre-shaped and/or pre-shapable so that its application face adapts at least in part to the shape of the movable upper eyelid.

In particular, the patch may present an application face of shape that is selected, prior to application, as a function of the topology of the movable upper eyelid.

By way of example, the patch may be shaped in a factory, or at a point of sale, or at its site of use, by cutting out, machining, molding, compression, hot-forming, or in some other way. The final shape of the patch before it is put into place may optionally be given by a shaping machine made available to the user of the patch.

In a variant, the patch may present an application face of shape, prior to application, that is independent of the shape of the movable upper eyelid, and the patch may be capable of taking on a shape that matches that of the movable upper eyelid after application, and then of conserving said shape after application, independently of the movable upper eyelid. In other words, once the application face has been given its shape, this shape may be conserved even in the absence of the eyelid. For example, the patch may present plasticity than enables it to deform in contact with the eyelid with the deformation to which it is subjected being non-elastic.

A plurality of patches of different sizes and/or shapes may be available to the user, e.g. presented within common packaging, and the user may select from those patches the patch that is most suitable for the desired effect. The user may proceed by successive approximations or on the advice of an expert. Where appropriate, the packaging of the patches may include one or more templates, e.g. serving to evaluate the curvature and/or the dimensions of the eyelid, e.g. curvature in a horizontal plane and curvature in a vertical plane.

The patch may be elongate in shape. For example, the patch may have a "half-moon" or "crescent-moon" shape in longitudinal section, with its outline in longitudinal section being formed for example by uniting two non-concentric circular arcs, optionally both concave on the same side, optionally both having the same radius. Thus, the outline of the patch, in longitudinal section, may correspond to uniting two circular arcs that are concave on the same side and of different radii, the circular arcs corresponding respectively to the application face and to the outside face.

In longitudinal section, the patch may also present a shape that is substantially rectangular, triangular, semi-elliptical, parabolic, or semicircular.

The patch may present a length that is substantially equal to the width of the movable upper eyelid and a width that is substantially equal to the height of the movable upper eyelid, but other dimensions are possible. The application face of the patch may optionally cover substantially all of the surface of the movable upper eyelid. The patch may optionally present a shape that is symmetrical about a plane of symmetry or an axis of symmetry. The height of the patch preferably occupies more than one-third of the height of the movable upper eyelid, and more preferably more than one-half of the height of the movable upper eyelid.

Prior to application, the application face of the patch may have a predefined non-plane shape with double curvature, or in a variant it may have an application face that extends in a plane prior to application.

When the application face of the patch is of a predefined non-plane shape with double curvature prior to application, said application face is concave towards the eyelid. The application face of the patch may present at least one spheroidal portion, in particular a portion that is spherical, ellipsoidal, paraboloidal, or hyperboloidal.

The application face of the patch, and in particular its spheroidal portion, may have a radius of curvature lying in the range 1.2 centimeters (cm) to 1.6 cm.

The application face of the patch may have double curvature, each of its curvatures presenting a radius of curvature lying in the range 1.2 cm to 1.6 cm, with it being possible for the radii of curvature to be different.

The application face of the patch, and in particular of its spheroidal portion, may have curvature that is determined by a given geometrical function, e.g. a function that is spherical, ellipsoidal, paraboloidal, or hyperboloidal, or in a variant it may have curvature that is not determined from a geometrical function. In particular, its curvature may be adapted to the shape of the movable upper eyelid, e.g. to the shape of the eyelid of an individual on whom the patch is applied, to the shape of the eyelid of an individual used as a reference, to the mean shape of the eyelids of a plurality of individuals, or indeed to the shape of an eyelid that corresponds to a canon of beauty.

The application face of the patch, and in particular the spheroidal portion, may include at least two non-coplanar plane facets, preferably at least six non-coplanar plane facets. The shape and/or at least one curvature of the application face of the patch may be dimensioned as a function of the dimensions of the facets and of the angles formed between the normals to said facets.

The thickness of the patch, in particular in the spheroidal portion, and as measured between the application face of the patch and the outside face thereof opposite to the application face may lie in the range 1 micrometer ($\mu$m) to 1 millimeter (mm), and preferably in the range 5 $\mu$m to 200 $\mu$m.

The thickness of the patch and/or the stiffness of the patch may vary along at least one axis of the patch, e.g. the longitudinal axis of the patch, or along an axis that is perpendicular or oblique relative to the longitudinal axis of the patch.

The patch may present resilience that varies as a function of position on the patch, e.g. associated with variation in the thickness of the patch.

The thickness of the patch may vary while the stiffness of the patch is constant. In a variant, the stiffness of the patch may vary, e.g. by using reinforcing elements, while the thickness of the patch is constant.

The thickness and/or the stiffness of the patch may be smaller in its central portion than at the edges of the patch, in particular at the longitudinal ends of the patch. In a variant, the thickness and/or the stiffness of the patch may be higher in the central portion than at the edges of the patch, in particular at the longitudinal ends of the patch.

The thickness and/or the stiffness of the patch may vary monotonically, e.g. decreasing or increasing, from one end of the patch to the other or from the middle of the patch towards the longitudinal ends thereof.

The patch may present periodic or irregular variations in thickness and/or stiffness, from one end of the patch to the other, in particular from one longitudinal end to the other.

The patch may present at least one localized zone of thickness and/or stiffness that differs from the remainder of the patch, and in particular from one longitudinal end to the other.

In particular in its spheroidal portion, the stiffness of the patch may lie in the range 200 kilopascals (kPa) to 200 gigapascals (GPa), and preferably lies in the range 1 megapascal (MPa) to 10 GPa.

Between at least two zones of the patch, its stiffness may vary by a factor of at least 2, e.g. by a factor of 5. The thickness of the patch between at least two zones of the patch may vary by a factor of at least 1.25, e.g. by a factor of 2.

The stiffness of the patch may vary, with the differences in stiffness being obtained in particular by using at least two materials of different stiffnesses, by adding at least one reinforcing element, by differing concentration of at least one compound in the patch, and/or by different treatment of at least two zones of the patch.

The thickness of the patch may vary, with the different thicknesses being obtained, for example, by molding the patch in a mold of varying thickness, by machining the patch to obtain varying thickness, by adding and/or removing material, by localized compression, and/or by printing in three dimensions.

The stiffness and/or the thickness of the patch may be modified after application to the eyelid, in particular by applying pressure, by relative movement between at least two component parts of the patch, in particular by movement of at least two sheets of the patch that are movable relative to each other, by applying heat and/or light, e.g. in order to harden, soften, and/or expand the material of the patch in optionally localized manner (e.g. by photocuring, thermosetting, and/or expanding material by applying heat), by adding and/or removing material, e.g. local application of one or more reinforcing elements, or by contact with a predefined reagent.

The patch may be flexible or rigid, plastic or elastic. The material, the thickness, and/or the stiffness of the patch may be selected to impart thereto characteristics that are appropriate for making the patch easier to handle, in particular for putting the patch into place and/or removing it.

The patch may be made of at least one polymer material, or some other synthetic material such as:
- a polyolefin, in particular polyethylene, polypropylene, polyisoprene, polystyrene, polybutadiene, polyacrylate, or polyacrylamide;
- a polymer obtained by condensation reactions, e.g. a polyester, a polyurethane, a polyamide, a polyurea, or some other organic or organomineral polymer, e.g. a polyether, silicone, a natural polymer such as a polyose (e.g. cellulose), a protein; or
- a wax;

among others.

The patch may be made of a mineral and/or metallic material, such as:
- a metal, alkaline earth, or alkali oxide, carbide, nitride, carbonate, phosphate, or sulfate, e.g. calcium carbonate or calcium phosphate;
- a silicate, an aluminosilicate; or
- a metal or an alloy based on iron, aluminum, titanium, magnesium, silver, gold, or platinum;

among others.

The patch may be made from a material including natural fibers, a fabric or other woven form, a paper or other non-woven form, wood, biocellulose, among others.

The patch may be made of a pure material or of a material mixed with some other material.

The patch may be made after taking imprints or measurements of the skin of the user, e.g. by performing three-dimensional (3D) acquisition of the relief of the eyelid by means of an optical or acoustic acquisition system, e.g. a stereoscopic vision, fringe projecting, ultrasound, or other system, e.g. a mechanical feeler.

The relief may be acquired in static or dynamic manner, with the eyes closed and/or with movement relative to the eyelids.

Where appropriate, acquisition may be performed using one or more predefined patches that are placed on the eyelid in order to determine the effect of those patches on the look and the mechanical behavior of the eyelid.

The patch may be cut out from a base structure. By way of example, the base structure may be made of a plastics material. For example, the base structure may comprise one or more spheroidal shapes, in particular shapes that are spherical, from which the patch(es) is/are cut out. The diameter of the spheroidal shape may be close to the diameter of the eye. In particular, the diameter of the spheroidal shape may lie in the range 26 mm to 28 mm.

The patch may comprise sheets of the same material, or of different materials. For example, the patch may be made by laminating sheets together. Adhesion between the sheets may be provided for example by electrostatic coupling or by surface tension or by using an adhesive. The sheets may optionally be movable relative to one another.

The patch may be made of a material that is not homogeneous, in particular a material that includes particles, fibers, flakes, or vacuoles, voids, and/or bubbles that are imprisoned or that connect to one another.

The patch may be porous to oxygen, air, and water vapor so as to enable the eyelid to breathe.

The patch may comprise an expandable material.

The application face of the patch, and/or the opposite face of the patch, may be smooth or may present roughness, cells, and/or asperities.

The application face of the patch, and/or preferably the opposite face of the patch, may simulate human skin, in particular the skin of the eyelid. In particular, it may present the same color, the same texture, and/or the same relief as the skin of the eyelid prior to application, or of a reference skin, e.g. satisfying certain beauty criteria. The surface of the application face of the patch and/or of its opposite face, may impart a soft or velvety appearance close to that of skin. The surface may be rough, e.g. presenting a succession of hollows and/or projections.

The patch may optionally be colored. The patch may have a single color or it may have multiple colors. The patch may present a color that is close to that of human skin. The patch may be transparent and/or translucent, enabling the skin of the eyelid to be observed through the patch. The patch may thus enable the appearance of the outline of the eye to be modified while being practically invisible to the eyes of an observer.

The patch may present a glossy or a mat effect. Glossiness may give the patch an attractive effect, in particular for young people, whereas a mat appearance may serve to make the patch more discrete, in particular for older people.

The surface state of the outside face of the patch, opposite from its application face, may be sufficiently rough to enable makeup to adhere to the eyelid.

Where appropriate, the patch may be provided to the user together with at least one makeup that is compatible with being applied to the outside face of the patch, which makeup may for example be contained in the same packaging as the patch.

The patch may present a length, measured along its curvilinear long axis, that lies in the range 2 cm to 3 cm. The patch may present a width, measured along its short axis, lying in the range 3 mm to 10 mm. The patch may present a ratio of greatest dimension over smallest dimension other than its thickness lying in the range 2 to 10.

The patch may include an optionally through recess in the application face of the patch and/or in its face opposite to the application face. In particular, the recess may be a through recess enabling makeup to be applied directly to the eyelids, for example. The recess may also improve comfort by making the patch better aired.

The recess may be substantially elongate in shape, in particular in the long direction of the patch, and for example it may be situated close to the eyelashes once the patch is applied to the movable upper eyelid.

By way of example, the recess may enable an eyeliner to be applied directly to the movable upper eyelid. For example, the recess may be a slot formed through the patch. The patch may serve as a stencil for applying the eyeliner. The material of the patch may be selected in such a manner that the eyeliner does not stay in place on the patch. Thus, eyeliner smudges on the patch are easily removed so as to leave a well-defined line on the eyelid.

The recess may also serve to insert at least some of the eyelashes therein, e.g. to impart predefined curvature thereto. The method of applying the patch may then include a step consisting in inserting the eyelashes through the recess in the patch, possibly while using a guide.

The patch may also have no contact with the eyelashes once it is in place on the eyelid.

The outside face opposite from the application face of the patch may be covered at least in part in makeup, e.g. makeup that is colored, glossy, or mat. As a result, the invention may serve to change the appearance of the outline of the eye, e.g. by increasing the glossiness, the appearance, and/or the color of the eyelid.

The patch may include a colored pattern and/or print simulating a line of eyeliner.

It may thus be possible to increase the visibility of the movable upper eyelid and to contribute to improving the appearance of the eye. The shape of the application face of the patch, before or after application, may make it possible to obtain better effects, e.g. in comparison with applying a flat strip on the eyelid. Furthermore, the good behavior of the patch of the invention over time may serve to avoid the patch becoming accidentally unstuck, which would reveal unattractive appearance on the eyelid as a result of using makeup.

The outside face of the patch opposite from its application face may include a zone for holding eyelashes and/or false eyelashes. The holding zone may serve to constrain the user's eyelashes so as to give them predefined curvature. The holding zone may correspond to a through slot as described above, into which the eyelashes may be inserted.

It is also possible to place false eyelashes on the holding zone on the patch, in particular on the outside edge of the application face of the patch and/or on its opposite face. The holding zone may be reinforced and/or may be of greater thickness.

In addition to modifying the shape of the eyelid when that is desired, there are numerous other applications for a patch of the invention.

The patch may serve to obtain a symmetrical appearance for the eyelids for both eyes of an individual.

The patch may also serve to mask at least in part one or more defects of the movable and/or stationary upper eyelid, such as for example an excrescence, a visible vein, or a beauty spot.

The patch may facilitate application of a care active agent for the eye or for the eyelid, and may include such an active agent. In particular, the patch may be used as a reservoir for applying a composition on the movable and/or stationary upper eyelid. By way of example, the patch may be made of a porous material impregnated with an active agent. For example, the patch may release an active agent for care or growth of eyelashes, e.g. bimatoprost, for anti-aging treatment of the eyelid, for providing comfort for the eye, e.g. using water, a physiological liquid, an active agent against irritation, an anesthetic, an active agent against dust, among others. The applied active agent may be a cosmetic without any therapeutic action.

The active agent may be incorporated in the patch prior to application thereof and/or it may be incorporated in the patch at the time it is applied and/or after application. The active agent may be incorporated in the position with or without solvent.

When the patch contains an active agent, the patch may be proposed to the user in sealed packaging, e.g. sterile packaging.

The patch may also enable secretions to be retained, e.g. sweat and/or sebum.

The patch may also enable the movable and/or fixed upper eyelid to be protected against the effects of light, e.g. sunlight, of wind, and/or of intrusion by particles, e.g. of sand.

The patch may include a patch grip part. The grip part may be plane and connected to the remainder of the patch in flexible manner, e.g. via a hinge connection, at the edge of the patch. The grip part of the patch may comprise a non-spheroidal portion. The grip part of the patch may for example facilitate putting the patch into place and/or removing it. Where appropriate, the grip part may be defined by a removable portion of the patch. The grip part of the patch may bear against the stationary upper eyelid.

The patch may include a part that is arranged to bear, at least in part, against the eyelashes of the eye, in order to act mechanically, biologically, and/or chemically on the eyelashes. The part arranged to bear against the eyelashes of the eye may be plane, and may be connected in flexible manner, in particular via a hinge connection, to an edge of the patch. The part arranged to bear against the eyelashes of the eye may, where appropriate, include a slot to enable the curvature of the eyelashes to be modified at least in part, as described above for the zone for holding eyelashes and/or false eyelashes on the face opposite to the application face of the patch.

The grip part of the patch and/or the part arranged to bear against the eyelashes may optionally be made of the same material as the remainder of the patch, and may optionally be of the same thickness. They may be made of a material that is different from the remainder of the patch, e.g. being heat-sealed, adhesively bonded, overmolded, and/or mechanically assembled with the remainder of the patch.

The patch may be fabricated by thermoforming, by molding, by three-dimensional polymerization, by laser etching, by mechanical machining, among others.

The application face of the patch and/or the movable upper eyelid may be covered at least in part in a compound facilitating adhesion of the patch to the movable upper eyelid. The compound may be an adhesive, in particular a pressure sensitive adhesive (PSA). The compound may be applied prior to putting the patch into place, on the eyelid and/or on the patch. The compound may be applied by the user, where appropriate. The compound may also be present on the patch when it is supplied to the user.

The adhesive power of the adhesive compound covering at least part of the application face of the patch and/or the movable upper eyelid may be reduced by adding some other compound. The compound may be covered by a removable non-stick protective film, where appropriate.

The patch may include a non-adhesive portion defining at least a portion of the application face.

The compound enabling the patch to adhere to the eyelid need not be adhesive, for example it may be a gel, a cream, a solvent, or an oil, optionally including an active agent, and serving to impart sufficient adhesion to the patch by the surface tension effect to hold it on the movable upper eyelid.

Retention of the patch may also be improved by appropriately selecting the material and/or the shape of the application face of the patch. For example, the application face of the patch may be covered in a non-slip material, e.g. an elastomer.

Where appropriate, the compound applied to the movable upper eyelid may react with the material from which the patch is made. The compound applied to the movable upper eyelid may for example be a silicone having reactive functions such as hydrosilylation functions or a cyanoacrylate monomer.

Where appropriate, the compound may cover certain zones only of the application face of the patch and/or of the movable upper eyelid, e.g. zones situated at the margins of the patch and/or of the movable upper eyelid.

Prior to application, the patch may be made pre-shapable in various ways.

The patch may be made of a soft material that is reshapable, e.g. a plastics material or a material suitable for being cured.

By way of example, the patch may present hardness that varies over time, preferably that increases, as a result of a stimulus, e.g. radiation, the application of a liquid, evaporation, the application of heat, a chemical or biological reaction, among others.

The patch may also be made of a material having shape memory, in particular being made in such a manner as to be capable of taking its final shape at the time of application.

The patch may be made of a film-forming polymer material, e.g. based on reactive silicone.

The patch may include an extension at least of its longitudinal ends, the extension being for application to the cavity at the inner corner of the eye and/or on the end of the eye remote from said cavity. Such an extension may enable a pleasing effect to be applied to the eye by extending the fold of the eye.

The extension may be substantially flat and have a predefined non-plane shape. In particular, the extension may be flat when it is for placing over the cavity in the corner of the eye. Conversely, the extension may have a predefined non-plane shape, in particular a spheroidal shape, when it is for placing over the end of the eye that is opposite from the corner of the eye.

The extension may also be made of a material that is more flexible than the remainder of the patch, in particular to make it easier to place over the cavity at the corner of the eye and/or over the end opposite therefrom.

The extension may optionally be made of the same material as the remainder of the patch. The extension and the remainder of the patch may be molded as a single piece.

The extension may have thickness lying in the range 10 μm to 1 mm, for example.

Where it is connected to the remainder of the patch, the extension may form a constriction in the width direction of the patch. This constriction may form a hinge making it easier to change the slope of the patch in the region of the corner of the eye.

The extension may be covered at least in part and/or may include a makeup and/or care product.

As mentioned above, the method of the invention may include a step consisting in acquiring the topology of the outline of the eye prior to applying the patch. The patch may be pre-shaped as a function of the result of acquiring the topology of the outline of the eye.

By way of example, the method may be implemented with an analysis system enabling the shape of the outline of the eye to be analyzed, in particular the shape of the movable upper eyelid and/or the stationary upper eyelid, and enabling the shape for the patch to be deduced, in particular the shape of its application face for placing on the movable upper eyelid, so as to obtain a desired modification to the appearance of the outline of the eye.

Independently or in combination with the above, the invention thus also provides a system for analyzing the topology of the outline of the eye in order to implement the above-defined method.

The system may also be configured to identify the portion(s) of the stationary and/or movable upper eyelid for modification in order to approach a standard eyelid shape, e.g. corresponding to a canon of beauty, a shape desired by the user, e.g. corresponding to the shape of the user's eye when young, or indeed a shape resulting from the mean of evaluations performed on a plurality of people or corresponding to an age group and/or to a given population type, among others.

In particular, the system may be configured to determine the portion(s) of the movable and/or stationary upper eyelid that is/are not within the regularity of curvature presented by most stationary and/or movable upper eyelids of certain people, in particular young people.

The system may in particular be configured to identify the portion(s) of the stationary upper eyelid that has/have drooped. The system may also serve to identify the recessed portion(s) of the movable and/or stationary upper eyelid.

The system may operate by simulation. Thus, it may be provided with calculation means such as a microcomputer or a server capable of simulating the rendering of the outline of the eye after the patch has been applied. By way of example, such means may operate by having recourse to a database and/or on the basis of logic for applying stresses to a soft body, for example.

By comparison, the system may deduce the patch(es) closest to a target shape, e.g. depending on the desires of the user or depending on an appearance model.

The system may also operate by deduction and by calculation. For example, the system may deduce the shape and/or the stiffness of the patch, e.g. to correspond to a target shape, e.g. on the basis of the user's desires or on the basis of an appearance model. In particular, the deduction may be performed on the basis of the logic of applying stresses to a soft body, or on the basis of a database, e.g. derived from acquired experience.

Preferably, the system is configured to make it possible to select from among the simulated and/or calculated patch(es) the patch or patches that procure the best comfort, and in particular that present the smallest thickness.

The system may be provided with a user interface. The interface may for example serve to receive input concerning the final shape desired for the outline of the eye, the simulated or deduced final shapes, the estimated comfort of the patch(es), or indeed a final shape selection from among the simulated final shapes.

The system may be distributed as a plurality of separate elements, or it may be integrated as a unit. Where appropriate, data may be transmitted to a predefined calculation unit, or over a connection to a server.

The system may also serve to capture the shape of the eye, e.g. by image capture.

The system may serve to cut out and/or make the patch (es), or where appropriate to order them.

The system may include means for receiving input about the result obtained with the patch, e.g. a questionnaire that is displayed on a screen.

The system may include means making it possible progressively to refine its tools for simulation, and/or for deduction, and/or its models, optionally in individualized manner.

The system may serve to optimize the color rendering of the outline of the eye and/or the texture rendering of the outline of the eye.

The system may also serve to generate more or less detailed advice about makeup suitable for use.

The system may be configured to compare both eyes so as to correct a problem of asymmetry between the eyes. The system may for example compare both eyes in order to deduce whether or not they are symmetrical. The system may for example identify the eye which is the more closed on the basis of image analysis.

The system may perform one or more image acquisitions, in particular as a function of the degree to which the eye is open (e.g. of the eye when closed so as to be half-open and when open) in order to acquire the topology of the eye and provide assistance in selecting and/or designing the patch.

A practitioner may also have some predefined number of different standard patches that can be tried out on a user in order to determine the patch that is the most appropriate.

The method of the invention may comprise one or more steps, optionally performed in succession, consisting in using the above-described analysis system.

Independently or in combination with the above, exemplary embodiments of the invention also provide a patch for modifying the appearance of the outline of the eye, the patch having a non-plane application face that is preshaped with curvature about at least two mutually perpendicular curvature axes.

Independently or in combination with the above, exemplary embodiments of the invention also provide a kit comprising:

a patch, as defined above, presenting an application face of predefined non-plane shape with multi-dimensional curvature prior to application of the patch on the movable upper eyelid, and/or a patch presenting an application face tending to conserve the shape into which it is put by modifying a curvature of the patch after applying it to the movable upper eyelid, and independently of the movable upper eyelid; and a makeup and/or an adhesive and/or an active composition for applying, in particular extemporaneously, to the application face of the patch, to the opposite face of the patch, and/or to the movable upper eyelid.

The patch may present double curvature.

Independently or in combination with the above, exemplary embodiments of the invention also provide a kit comprising:

a patch, as defined above, presenting an application face of predefined non-plane shape with multi-dimensional curvature prior to application of the patch on the movable upper eyelid, and/or a patch presenting an application face tending to conserve the shape into which it is put by modifying a curvature of the patch after applying it to the movable upper eyelid, and independently of the movable upper eyelid; and an eyeglass frame and/or at least one correction lens adapted to the user's vision.

Such a kit enables the look to be modified, e.g. by matching the color of the lens or of the frame to the color of the patch.

Independently or in combination with the above, exemplary embodiments of the invention also provide a kit comprising:

a first patch of the invention, presenting an application face of predefined non-plane shape with multi-dimensional curvature prior to application of the patch on the movable upper eyelid, and/or a patch presenting an application face tending to conserve the shape into which it is put by modifying a curvature of the patch after applying it to the movable upper eyelid, and independently of the movable upper eyelid; and a second patch, also of the invention, with the shape of its application face differing from that of the first patch and/or with stiffness and/or thickness that differ from the stiffness and/or thickness of the first patch.

This may enable the user to apply the patch that is most appropriate for the desired result.

DESCRIPTION OF THE FIGURES

The invention can be better understood on reading the following description of non-limiting implementations thereof, and on examining the figures of the diagrammatic and fragmentary figures of the drawings, in which:

FIGS. 4A to 4C show the possibility of modifying the stiffness and/or the thickness of a patch suitable for use in the method of the invention, by expanding material by applying heat;

FIGS. 5A to 5D show examples of patches used in the method of the invention, in longitudinal section;

FIGS. 6A to 6I show other examples of patches used in the method of the invention, presenting varying thicknesses and/or stiffnesses;

FIG. 7 shows the possibility of using reinforcing elements within a patch in order to modify its stiffness, without requiring its thickness to be modified;

FIGS. 8A to 8C are diagrams showing the possibility of a patch that is usable in the method of the invention including at least one extension at one end;

FIGS. 9 and 10 show respectively the possibility of a patch of the invention including a grip portion and a portion for bearing against the eyelashes;

FIGS. 11a and 11b show examples of patches of the invention presenting respective recesses;

FIGS. 12 and 13 show the use of a patch to modify the look of an eye;

FIGS. 1A and 1B are diagrammatic section views showing examples of the relative positioning of the stationary and movable upper eyelids 3 and 2 of the eye 4, when the eye is closed (FIG. 1A) and when the eye is open (FIG. 1B).

Figure 1A:
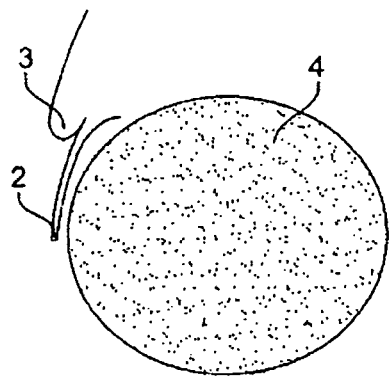
FIGS. 1A and 1B show respective examples of relative positioning between the stationary and moving upper eyelids of the eye while the eye is closed and while the eye is open, without using the patch of the method of the invention.
Figure 1B:
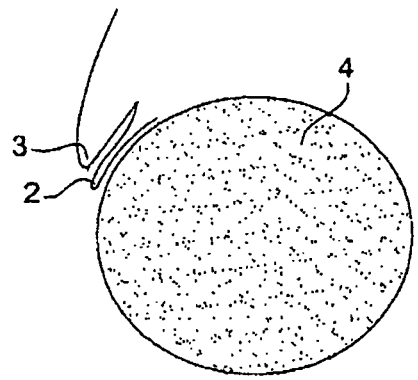

By comparing FIGS. 1A and 1B, it can be seen that when the eye 4 is closed (FIG. 1A), the movable upper eyelid 2 covers the pupil of the eye.

When the eye 4 is open (FIG. 1B), it can be seen that the stationary upper eyelid 3 droops so as to cover the movable upper eyelid 2, at least in part. This phenomenon, often due to a person aging, has an undesirable effect and it is generally desirable to be able to correct it.

Figure 2A:
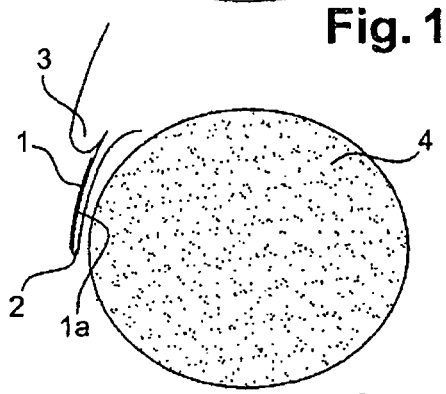
FIGS. 2A and 2B show respective examples of relative positioning of the stationary and moving upper eyelids of the eye when the eye is closed and when the eye is open, while using the patch of the invention.
Figure 2B:
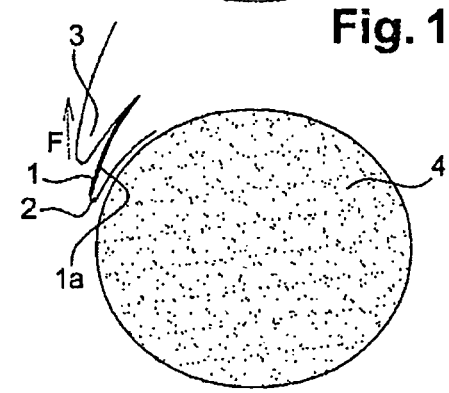

FIGS. 2A and 2B correspond respectively to the open or closed position of the eye 4 in FIGS. 1A and 1B. Nevertheless, a patch 1 has been applied on the movable upper eyelid 2.

The patch 1 may include an application face 1a of predefined non-plane shape presenting double curvature before application, and/or an application face 1a that tends to retain the shape into which it has been put, by modifying a curvature of the patch after it has been applied to the movable upper eyelid 2, independently of the movable upper eyelid 2.

The patch 1 is applied to the movable eyelid 2 while the eye 4 is closed. When the eye 4 is opened (FIG. 2B), the patch 1 contributes to reducing the droop of the stationary upper eyelid 3, with the patch 1 making it possible to modify the relative position of the stationary upper eyelid 3 relative to the movable upper eyelid 2 by lifting it in the direction of arrow F.

Figure 3A:
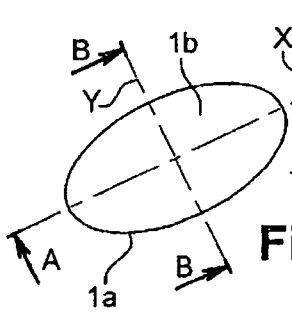
FIGS. 3A to 3E show examples of patches used in the method of the invention.
Figure 3B:
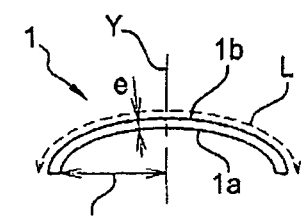
Figure 3C:
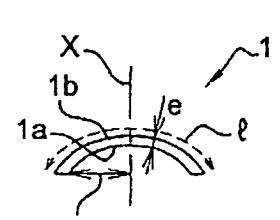

FIGS. 3A to 3C show a first variant embodiment of the patch 1. FIG. 3A is a perspective view of the patch 1, FIG. 3B is a longitudinal section view on AA of the FIG. 3A patch 1, and FIG. 3C is a cross-section view on BB of the FIG. 3A patch 1.

In this example, the patch 1 presents an application face 1a of predefined non-plane shape with double curvature, the patch 1 presenting a spheroidal portion, for example. The application face 1a of the patch 1 may, for example, be curved along its longitudinal axis X and its transverse axis Y.

By way of example, the thickness e of the patch 1 may lie in the range 1 µm to 1 millimeter mm, and preferably lies in the range 5 µm to 200 µm. By way of example, the stiffness of the patch 1 lies in the range 200 kPa to 200 GPa, and preferably in the range 1 MPa to 10 GPa. In this example, the thickness e and the stiffness of the patch 1 are constant, but they need not be.

The radii of curvature $R_x$ and $R_y$ of the patch 1, as associated respectively with the curvature axes X and Y of the patch 1, may lie in the range 1.2 cm to 1.6 cm, for example.

As measured along its curvilinear long axis, the patch 1 may present a length L lying in the range 2 cm to 3 cm, and as measured along its short axis, it may present a width l lying in the range 3 mm to 10 mm.

Figure 3D:
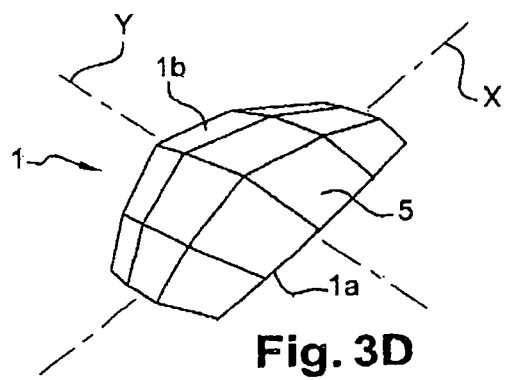

FIG. 3D shows another variant embodiment of the patch 1 suitable for use in the method of the invention and/or serving to model the patch 1 that is to be used in the method of the invention.

In this example, the patch 1 presents a spheroidal portion, e.g. having a plurality of non-coplanar plane facets 5.

Figure 3E:
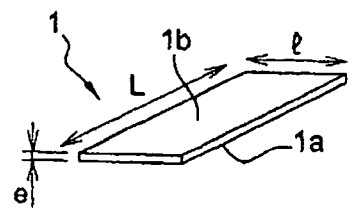

FIG. 3E shows a second variant embodiment of a patch 1 suitable for use in a method of the invention. In this example, the patch 1 is substantially plane in shape prior to application, and it presents an application face 1a that tends to conserve the shape into which the patch 1 is put by modifying a curvature of the patch 1 after it has been applied to the movable upper eyelid 2 by virtue of the plasticity of the patch 1, and for this to be independent of the movable upper eyelid 2.

The patch 1 may present a length L lying in the range 2 cm to 3 cm and a width l lying in the range 3 mm to 10 mm.

By way of example, the thickness e of the patch 1 may lie in the range 1 µm to 1 mm, and preferably lies in the range 5 µm to 200 µm. By way of example, the stiffness of the patch 1 lies in the range 200 kPa to 200 GPa, and preferably in the range 1 MPa to 10 GPa. In this example, the thickness e and the stiffness of the patch 1 are constant, but they need not be.

FIGS. 4A to 4C show the possibility of modifying the stiffness and/or the thickness of a patch 1 suitable for use in the method of the invention, by expanding material by applying heat. The stiffness and/or the thickness of the patch may be modified by expanding material either before or after the patch has been put into position on the movable upper eyelid.

The patch 1 may include an expandable material 40a present in all or part of the patch 1, as shown in FIG. 4A. The expandable material 40a may comprise expandable polymer spheres incorporating a solvent, e.g. spheres of Expansel®.

A heat source C may serve to heat the patch 1 locally, e.g. in a zone Z, as shown in FIGS. 4A and 4B, FIG. 4B showing the modification obtained in the zone Z after it has been heated.

It is also possible to place an expandable element of size smaller than the underlying layer of the patch in order to modify the thickness and/or the stiffness of the patch.

In order to avoid or reduce potential deformation in the thickness of the patch 1 or potential variation in the stiffness of the patch 1 while the source C is applying heat, it is possible to make the patch 1 as at least two parts 1' and 1", e.g. superposed parts as shown in FIG. 4C. The bottom part 1" may be made so as to be insensitive to the application of heat by the source C, e.g. being made in full or in part out of a material 40b that is not expandable by applying heat, while the top part 1' may comprise in full or in part a material 40a that is expandable by applying heat.

FIGS. 5A to 5D show examples of patches 1 in longitudinal section.

As can be seen, the patch 1 may present a shape in longitudinal section that may be of any type, e.g. rectangular with optionally rounded edges, triangular, or semicircular.

Optionally, the thickness e of the patch may vary. The examples of FIGS. 5A to 5D correspond to patches in which the application face 1a is shaped at the time of application. In variants that are not shown, the profile for variation in the thickness e in the longitudinal direction is as shown in FIGS. 5A to 5D, but the application face 1a is curved prior to being put into place about at least two mutually perpendicular axes of curvature X and Y, with the application face 1a being spheroidal, for example.

FIGS. 6A to 6I show other variant embodiments of patches 1.

The patch 1 may present thickness e that varies along a transverse axis Y of the patch 1, as shown in FIG. 6A, or along a longitudinal axis X of the patch 1, as shown in FIG. 6B to 6H.

In these figures, the patches 1 are shown flat, however the description below also applies to patches having application faces that are not plane, e.g. that are spherical.

The patch 1 may present periodic variation of thickness e, as can be seen in FIG. 6A.

By way of example, the variation in the thickness e of the patch 1 takes place in the transverse direction. Variation in the thickness e may give rise to longitudinal ribs being formed that project from the outside face 1b and/or from the application face 1a. The density of the material of the patch 1 may be uniform or it may be greater in the zones of smaller thickness, e.g. as a result of the patch 1 being compressed in said zones.

The thickness e of the patch 1 may also vary monotonically, e.g. increasing or decreasing, from one end of the patch 1 to the other, e.g. from one longitudinal end to the other, as can be seen in FIG. 6C.

The patch 1 may present a localized zone 13 of thickness e that is different from the remainder of the patch, as can be seen in FIG. 6B, e.g. a zone of localized increased thickness.

The thickness e of the patch 1 may be greater in its central portion than at the longitudinal ends of the patch, as can be seen in FIG. 6H, or it may be smaller in the central portion than at the ends of the patch, as can be seen in FIG. 6G. In this figure, a recess 14 is formed in the outside face 1b of the patch 1. In a variant, the recess is formed in the application face 1a.

The patch 1 may present thickness e that varies as a result of superposing a plurality of sheets 15, as can be seen in FIGS. 6D to 6F. These sheets 15 may be fastened relative to one another.

The use of a plurality of sheets 15, e.g. two sheets 15a and 15b as shown in FIG. 6I, may serve to increase the stiffness of the patch 1, for example. The sheets may be superposed exactly or otherwise. For example, the top sheet 15a need not cover the bottom sheet 15b completely.

In the embodiments of FIGS. 6A to 6I, the patch 1 may also present stiffness and/or thickness that varies along one or more axes other than the longitudinal axis X.

FIG. 7 shows the possibility of incorporating one or more reinforcing elements 6 in the patch 1 so as to modify its stiffness in one or more zones of the patch. By way of example, the reinforcing elements 6 are constituted by metal reinforcement, in particular by one or more wires having a diameter lying in the range 10 µm to 200 µm, by reinforcement constituted by rigid materials such as hard plastics, such as polyethylene threads, or ceramic threads.

FIG. 8A is a perspective view showing the possibility of having a patch 1 that includes extensions 7a and 7b. FIG. 8B is a diagrammatic face view of such a patch 1 including extensions 7a and 7b applied on the movable upper eyelid 2. FIG. 8C is a diagrammatic section view showing the patch 1 including an extension 7a applied on the cavity 16 at the corner of the eye.

By way of example, the extension 7a may be substantially plane in shape and may be designed to rest on the cavity 16 in the corner of the eye, next to the nose 17, whereas the extension 7b may present a shape that is substantially spheroidal for being placed on the end of the eye opposite from the cavity at the corner of the eye.

The extensions 7a and 7b may be more flexible than the central portion of the patch 1. The extensions 7a and 7b may optionally be made of the same material as the remainder of the patch 1.

Each extension 7a and 7b may co-operate with the body of the patch 1 to define respective constrictions R and R' in the width of the patch 1. Such a constriction R or R' may define a zone of increased deformability making it easier to obtain a break of slope between the extension and the body of the patch, as can be seen in FIG. 8C.

In the examples of FIGS. 8A to 8C, the patch 1 has two extensions 7a and 7b, but in a variant it could have only one extension 7a or 7b.

FIG. 9 is a diagrammatic perspective view showing the possibility of the patch 1 including a grip portion 8a, e.g. extending the outside face 1b opposite from the application face 1a. The grip portion 8a may have one of its edges 18 secured to an edge of the patch 1.

The grip portion 8a may be plane and come to bear against the stationary upper eyelid 3. Thus, the grip portion 8a may be flexibly connected to one of the edges of the patch 1, e.g. via a hinge connection, so as to be capable of adapting to the shape of the stationary upper eyelid 3 during application.

The grip portion 8a may make it easier to put the patch 1 into place on the movable upper eyelid 2, and/or to remove it. By way of example, the user may take hold of the patch 1 via the grip portion 8a in order to be able to put the patch 1 into position on the movable upper eyelid 2, and/or to remove it.

FIG. 10 shows the possibility of the patch 1 including a bearing portion 8b arranged to bear at least in part against the eyelashes. By way of example, the bearing portion 8b may serve to act mechanically, biologically, and/or chemically on the eyelashes, e.g. in order to administer a care product and/or makeup on the eyelashes in order to modify the curvature of the eyelashes, inter alia. For example, the bearing portion 8b may include a slot 19 into which the eyelashes may be inserted at least in part, e.g. in order to modify their curvature. The slot 19 may also act as the zone for handling the above-described false eyelashes and/or eyelashes for the face 1b that is opposite to the application face 1a of the patch 1. The bearing portion 8b may be plane and connected to the remainder of the patch 1 in flexible manner, e.g. via a hinge connection. Where appropriate, the bearing portion 8b may also serve as a grip portion as described above.

FIG. 11a shows the possibility of the patch 1 including a recess 9. The recess 9 may optionally be a through opening, and may serve for example to apply a makeup and/or care product to the movable upper eyelid 2.

In this example, the recess 9 is elongate in a transverse direction. In a variant, and as shown in FIG. 11b, the recess 9 may be elongate in a longitudinal direction and may for example be situated close to the border of the patch 1 that is to be applied close to the eyelashes, e.g. in order to enable an eyeliner to be applied or to enable eyelashes to be inserted in the recess 9 so as to constrain them to have some particular curvature, as described above with reference to FIG. 10.

Figure 14:
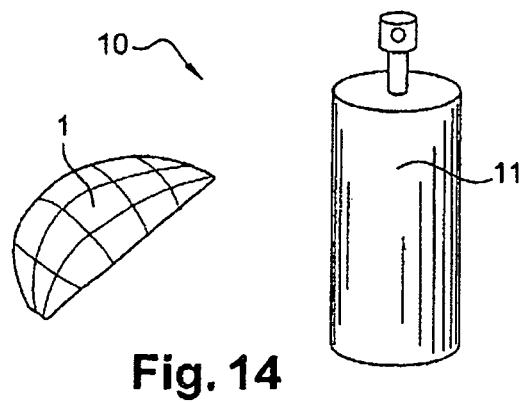
FIG. 14 shows an example of a kit of the invention.

FIG. 14 shows an example of a kit 10 of the invention.

By way of example, the kit 10 comprises a patch 1 as described in any of the above embodiments, and at least one container 11 containing makeup and/or an adhesive and/or an active composition, suitable for application to the application face 1a of the patch 1, to the face 1b that is opposite from the application face 1a, and/or to the movable upper eyelid 2.

In a variant or in combination, the kit may include an eyeglass frame and/or correcting lenses associated with the patch 1.

Figure 15:
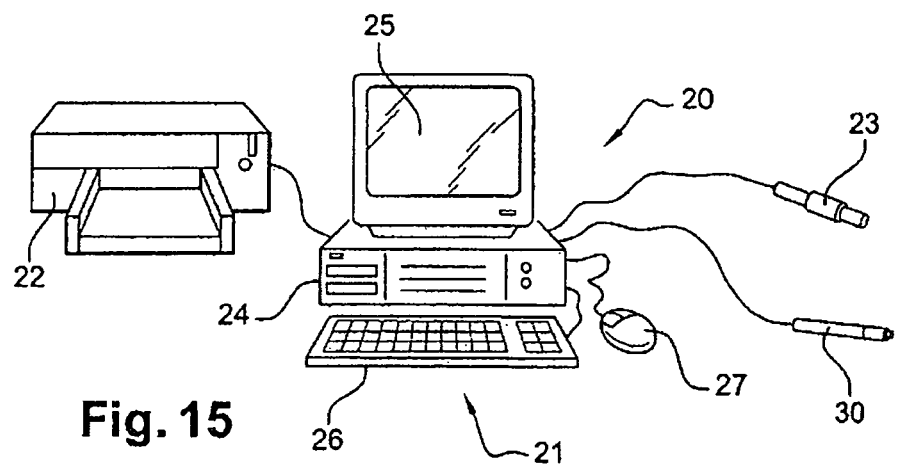
FIG. 15 shows an example of a system for analyzing the topology of the outline of the eye in order to implement the method of the invention.

FIG. 15 shows an example of an analysis system 20 for analyzing the topology of the outline of the eye in order to implement the method of the invention.

By way of example, the analysis system 20 may comprise a computer 21, a printer 22 connected to the computer 21, and a camera 23 enabling the topology of the outline of the eye to be acquired, the camera likewise being connected to the computer 21.

The computer 21 may be conventional and comprise a central unit 24, a screen 25, and a user interface including a keyboard 26 and a mouse 27.

The analysis system 20 may also include a unit 30 for shaping the patch. The unit 30 for shaping the patch may serve, for example, to modify the shape of the application face of the patch after acquisition of topology by the camera 23 and prior to applying the patch on the movable upper eyelid.

The analysis system 20 may be used as described above. For example, the analysis system 20 may serve to make a patch on the basis of measurements made of the skin of the user. The analysis system 20 may enable the relief of the eyelid to be captured in 3D by optical or acoustic acquisition, e.g. by stereoscopic vision, by projecting fringes, ultrasound, etc., e.g. by a mechanical feeler.

The relief may be acquired statically or dynamically, with the eyes closed and/or with movement relative to the eyelids.

Where appropriate, acquisition may be performed using one or more predefined patches placed on the eyelid in order to determine the effect of these patches on the look of the eye and on the mechanical behavior of the eyelid.

Figure 16:
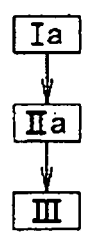
FIGS. 16 to 18 show examples of steps that may be implemented in the method of the invention.
Figure 17:
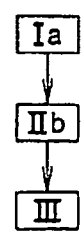
Figure 18:
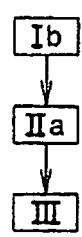

FIGS. 16 to 18 are diagrams showing examples of steps that may be implemented in the method of the invention.

By way of example, the method may include step Ia consisting in acquiring the topology of the outline of the eye, e.g. using an analysis system 20 as described above, followed by a step IIa consisting in selecting a patch that is appropriate for the topology of the eye from a range of available patches, and finally a step III consisting in applying the patch as selected in this way to the movable upper eyelid, as shown in FIG. 16.

For example, during step IIa, the user may have a plurality of patches of different sizes and/or shapes available, e.g. present within common packaging, and the user may select amongst these patches the patch that is the most suitable for the desired effect given the results of the topology acquisition. The user may proceed by successive approximations or on the advice of an expert. Where appropriate, the packaging of the patches may comprise one or more templates serving for example to evaluate the curvature and/or the dimensions of the eyelid, e.g. its curvature in a horizontal plane and in a vertical plane.

In a variant, as shown in FIG. 17, the method may comprise a step Ia consisting in acquiring the topology of the outline of the eye, followed by a step IIb consisting in fabricating a patch corresponding to the topology of the eye, and finally a step III consisting in applying the patch as fabricated in this way to the movable upper eyelid.

By way of example, during step IIb, the patch may be shaped in the factory, at a point of sale, or on the site of use, by cutting, machining, molding, compression, hot-forming, or in some other way, as a function of the results of acquiring the topology. The final shape of the patch prior to being put into place during step III may optionally be given by a shaping machine made available to the user of the patch.

In a variant, the patch may present an application face having a shape, prior to application, that is independent of the shape of the movable upper eyelid, and the user gives the patch a shape that is adapted to the shape of the movable upper eyelid after it has been applied thereto as a function of the results of the acquisition of topology, so as to conserve this shape after application, independently of the movable upper eyelid.

By way of example, the patch may be fabricated by being cut out from a base structure. By way of example, the base structure may be made of a plastics material and include one or more spheroidal shapes, in particular spherical shapes, from which the patch is cut out. The diameter of the spheroidal shape may be close to the diameter of the eye. In practice, the diameter of the spheroidal shape may lie in the range 26 mm to 28 mm.

FIG. 18 shows a method of the invention comprising step Ib consisting in having at least one patch available, e.g. in packaging, optional step IIa as described above consisting in selecting a patch adapted to the topology of the eye from a range of available patches suitable for modifying the desired change to the appearance of the outline of the eye, and step III consisting in applying the patch on the movable upper eyelid.

In above-mentioned step III of applying the patch on the movable upper eyelid, the patch may for example be applied with or without the help of adhesive and/or with or without the presence of a compound, e.g. an active agent, on the movable upper eyelid, on the application face of the patch, and/or on the face of the patch opposite to its application face.

Example

Hemispheroids were made out of a transparent polyethylene terephthalate (PET) material by a blowing technique. The hemispheroids presented a spherical shape with thickness of about 10 µm and a radius of curvature of about 14 mm.

Thereafter, scissors were used to cut patches out from the hemispheroids, the patches being of ovoid elongate shape in longitudinal section, of length (measured along a meridian), equal to 2.5 cm, 3 cm, or 3.5 cm, for example, and of greatest width (measured along a parallel) of up to 1.2 cm, and preferably of 1 cm.

A 50% branched sulfonic polyester polymer in solution in water, of the AC 1350® type sold by the supplier Eastman Chemicals, was deposited on the application face of the patches.

FIGS. 12 and 13 show two photographs illustrating the effect obtained on a person by using such a patch 1.

FIG. 12 shows the positioning of the transparent patch 1 on the movable upper eyelid 2 of the left eye (situated on the left when looking at the person). The patch 1 was applied while the movable upper eyelid 2 was closed.

The patch 1 may be held in place on the movable upper eyelid 2 with or without the use of an adhesive, or using a wetting composition, e.g. a hydrating cream or a gel.

In FIG. 13, there can be seen the effect obtained on the left eye after it has received the patch 1.

As can be observed by comparison with the right eye, the patch 1 serves to greatly reduce the droop of the stationary upper eyelid 3, such that it practically does not cover the movable upper eyelid.

The term "comprising a" is synonymous with "comprising at least one".

The invention claimed is:

1. A method of cosmetically modifying the appearance of the outline of the eye, the method comprising:
    applying at least one patch on a movable upper eyelid of the eye, an application face of the at least one patch having a predefined non-plane shape with multi-directional curvature before application of the at least one patch on the movable upper eyelid,
    wherein the multi-directional curvature is in at least two distinct planes about at least two distinct axes, and a thickness in a central portion of the at least one patch is smaller than a thickness at edges of the at least one patch.

2. A method according to claim 1, said at least one patch being pre-shaped or pre-shapable so that its application face matches at least in part the shape of the movable upper eyelid.

3. A method according to claim 1, the application face of the patch presenting at least one portion that is spheroidal.

4. A method according to claim 3, the at least one portion being spherical, paraboloidal, or hyperboloidal.

5. A method according to claim 1, said at least one spheroidal portion having a radius of curvature (Rx, Ry) lying in the range 1.2 cm to 1.6 cm.

6. A method according to claim 1, the thickness of the patch lying in the range 1 μm to 1 mm.

7. A method according to claim 6, the thickness of the patch lying in the range 5 μm to 200 μm.

8. A method according to claim 1, the stiffness of the patch lying in the range 200 kPa to 200 GPa.

9. A method according to claim 8, the stiffness of the patch lying in the range 1 MPa to 10 GPa.

10. A method according to claim 1, said at least one patch presenting a length lying in the range 2 cm to 3 cm, and a width lying in the range 3 mm to 10 mm.

11. A method according to claim 1, said at least one patch including an optionally-through recess in the application face of the patch and/or in its face opposite to the application face.

12. A method according to claim 1, the outside face of the patch opposite from its application face including a zone for holding eyelashes and/or false eyelashes.

13. A method according to claim 1, said at least one patch including an active agent for care of the eye or of the eyelid.

14. A method according to claim 1, said at least one patch including a part arranged to bear at least in part against the eyelashes.

15. A method according to claim 1, wherein the thickness of the patch measured between the application face of the patch and its face opposite to the application face, or the stiffness of the patch, varies along at least one axis of the patch.

16. A method according to claim 1, including acquiring the topology of the outline of the eye prior to applying the patch, said at least one patch being preformed as a function of the result of acquiring the topology of the outline of the eye.

17. A patch for modifying an appearance of an outline of an eye, the patch having a non-plane application face that is preformed with curvature about at least two mutually perpendicular axes of curvature (X,Y), a thickness of the patch being smaller in a central portion of the patch than at edges of the patch.

18. A kit comprising:
    a patch presenting an application face of predefined non-plane shape with multi-dimensional curvature in at least two planes about at least two distinct axes prior to application of the patch on a movable upper eyelid, a thickness in a central portion of the patch being smaller than a thickness at edges of the patch; and
    a makeup or an adhesive or an active composition for applying to at least one of the application face of the patch, to an opposite face of the patch, or to the movable upper eyelid.

19. A method of cosmetically modifying the appearance of the outline of the eye, the method comprising:
    applying at least one patch on a movable upper eyelid of the eye, the at least one patch being made of a material having a plasticity such that the at least one patch is configured to: (i) deform in a non-elastic manner in response to application of stress; and (ii) conserve the deformation in absence of the eyelid,
    wherein the applied stress causes the at least one patch to take up multi-directional curvature in contact with the eyelid, the at least one patch conserves said curvature when the applied stress ceases, and a thickness in a central portion of the at least one patch is smaller than a thickness at edges of the at least one patch.

20. A kit comprising:
    a patch presenting an application face tending to conserve a shape into which it is put by modifying a curvature of the patch after applying it to the movable upper eyelid, and independently of the movable upper eyelid, a thickness of the patch in a central portion of the patch is smaller than a thickness at edges of the patch; and
    a makeup or an adhesive or an active composition for applying to at least one of the application face of the patch, to an opposite face of the patch, or to the movable upper eyelid.

21. The method according to claim 1, the central portion comprising a zone of non-zero thickness, a thickness of the zone being smaller than the thickness of the edges of the at least one patch.

22. The method according to claim 19, the central portion comprising a zone of non-zero thickness, a thickness of the zone being smaller than the thickness of the edges of the at least one patch.

* * * * *